United States Patent
Karapetian et al.

(10) Patent No.: US 8,840,664 B2
(45) Date of Patent: Sep. 23, 2014

(54) HEART VALVE PROSTHESIS ANCHORING DEVICE AND METHODS

(75) Inventors: Emil Karapetian, Huntington Beach, CA (US); Chris J. Okos, Huntington Beach, CA (US); Matthew T. Winston, Ladera Ranch, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 56 days.

(21) Appl. No.: 13/517,810

(22) Filed: Jun. 14, 2012

(65) Prior Publication Data

US 2012/0323317 A1 Dec. 20, 2012

Related U.S. Application Data

(60) Provisional application No. 61/497,313, filed on Jun. 15, 2011.

(51) Int. Cl.
*A61F 2/24* (2006.01)

(52) U.S. Cl.
CPC ....... *A61F 2/2409* (2013.01); *A61F 2250/0063* (2013.01); *A61F 2220/0008* (2013.01); *A61F 2/2448* (2013.01); *A61F 2220/0033* (2013.01); *A61F 2220/0016* (2013.01)
USPC .......................... 623/2.17; 623/2.1

(58) Field of Classification Search
CPC ....... A61F 2/24; A61F 2/2475; A61F 2/2412; A61F 2/2418
USPC ............. 623/1.24, 2.26, 2.1, 2.11, 2.14, 2.17, 623/2.34, 2.36–2.4, 2.15
See application file for complete search history.

(56) References Cited

U.S. PATENT DOCUMENTS

| | | | |
|---|---|---|---|
| 3,143,742 A | 8/1964 | Cromie | |
| 3,574,865 A | 4/1971 | Hamaker | |
| 4,172,295 A | 10/1979 | Batten | |
| 5,397,346 A | 3/1995 | Walker et al. | |
| 5,554,185 A | 9/1996 | Block et al. | |
| 5,776,188 A | 7/1998 | Shepherd et al. | |
| 5,951,600 A | 9/1999 | Lemelson | |
| 6,059,827 A * | 5/2000 | Fenton, Jr. | 623/2.17 |
| 6,143,025 A | 11/2000 | Stobie et al. | |
| 6,176,877 B1 | 1/2001 | Buchanan et al. | |
| 6,273,875 B1 | 8/2001 | Siman et al. | |
| 6,287,339 B1 | 9/2001 | Vazquez et al. | |
| 6,419,696 B1 | 7/2002 | Ortiz et al. | |
| 6,458,156 B1 | 10/2002 | Wan et al. | |
| 6,585,766 B1 | 7/2003 | Huynh et al. | |

(Continued)

FOREIGN PATENT DOCUMENTS

| | | |
|---|---|---|
| EP | 2486894 A1 | 8/2012 |
| WO | 03/096932 A1 | 11/2003 |

(Continued)

*Primary Examiner* — Thomas J Sweet
*Assistant Examiner* — Christopher D Prone
(74) *Attorney, Agent, or Firm* — AnneMarie Kaiser; Guy Cumberbatch

(57) ABSTRACT

Apparatus and methods for securing heart valve repair or replacement prostheses in or near the heart. The apparatus and methods are particularly well suited for traditional surgery or minimally invasive surgery. The invention secures a heart valve repair or replacement prosthesis in place while lowering surgical exposure. The invention improves the ease of implantation because it reduces the number of surgical knots a clinician would normally tie in the limited space in and around the heart.

20 Claims, 17 Drawing Sheets

(56) References Cited

U.S. PATENT DOCUMENTS

| | | |
|---|---|---|
| 6,716,243 B1 | 4/2004 | Colvin et al. |
| 6,719,790 B2 | 4/2004 | Brendzel et al. |
| 6,730,118 B2 | 5/2004 | Spenser et al. |
| 6,790,229 B1 | 9/2004 | Berreklouw |
| 6,846,325 B2 | 1/2005 | Liddicoat |
| 6,958,076 B2 | 10/2005 | Acosta et al. |
| 7,011,094 B2 | 3/2006 | Rapacki et al. |
| 7,172,625 B2 | 2/2007 | Shu et al. |
| 7,175,659 B2 | 2/2007 | Hill et al. |
| 7,381,218 B2 | 6/2008 | Schreck |
| 7,717,955 B2 | 5/2010 | Lane et al. |
| 7,727,276 B2 | 6/2010 | Machiraju |
| 8,021,421 B2 | 9/2011 | Fogarty et al. |
| 8,142,497 B2 | 3/2012 | Friedman |
| 2002/0058994 A1 | 5/2002 | Hill et al. |
| 2005/0033344 A1 | 2/2005 | Dillard et al. |
| 2005/0075720 A1* | 4/2005 | Nguyen et al. ............... 623/1.26 |
| 2005/0137687 A1 | 6/2005 | Salahieh et al. |
| 2005/0220882 A1 | 10/2005 | Pritchard et al. |
| 2005/0283231 A1 | 12/2005 | Haug et al. |
| 2006/0004442 A1 | 1/2006 | Spenser et al. |
| 2006/0009841 A1* | 1/2006 | McGuckin et al. .......... 623/2.38 |
| 2006/0195185 A1 | 8/2006 | Lane et al. |
| 2006/0241748 A1* | 10/2006 | Lee et al. .................... 623/2.37 |
| 2010/0191327 A1 | 7/2010 | Lane et al. |
| 2011/0282438 A1* | 11/2011 | Drews et al. ................ 623/2.11 |

FOREIGN PATENT DOCUMENTS

| | | |
|---|---|---|
| WO | 2007/081820 A1 | 7/2007 |
| WO | 2009-084027 A2 | 7/2009 |
| WO | 2009113964 A2 | 9/2009 |

* cited by examiner

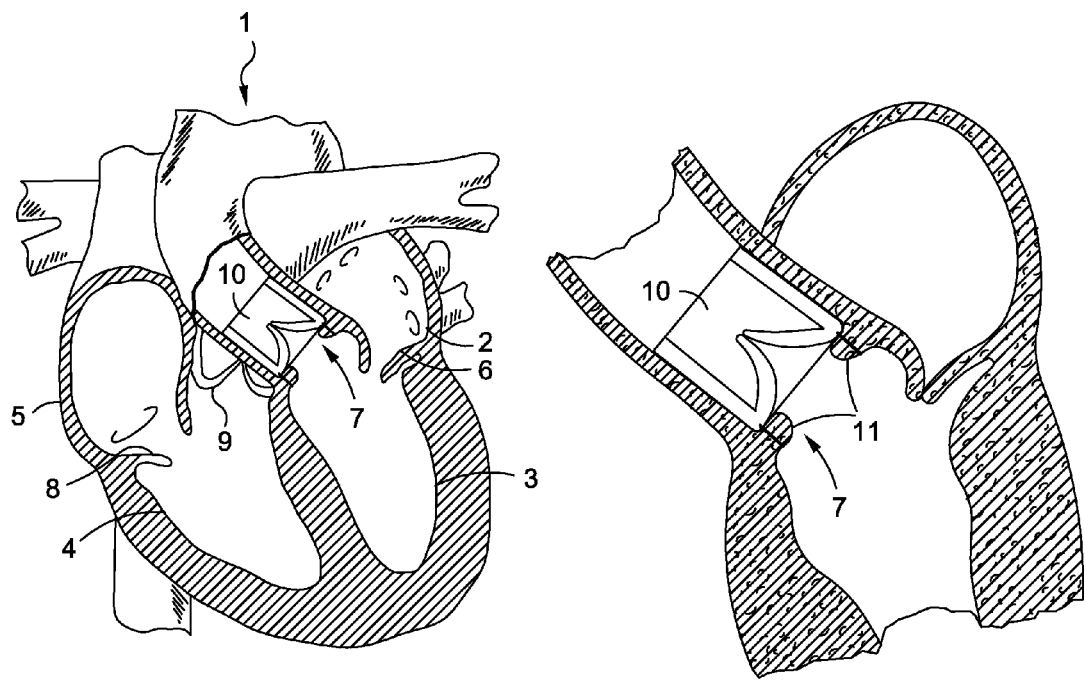
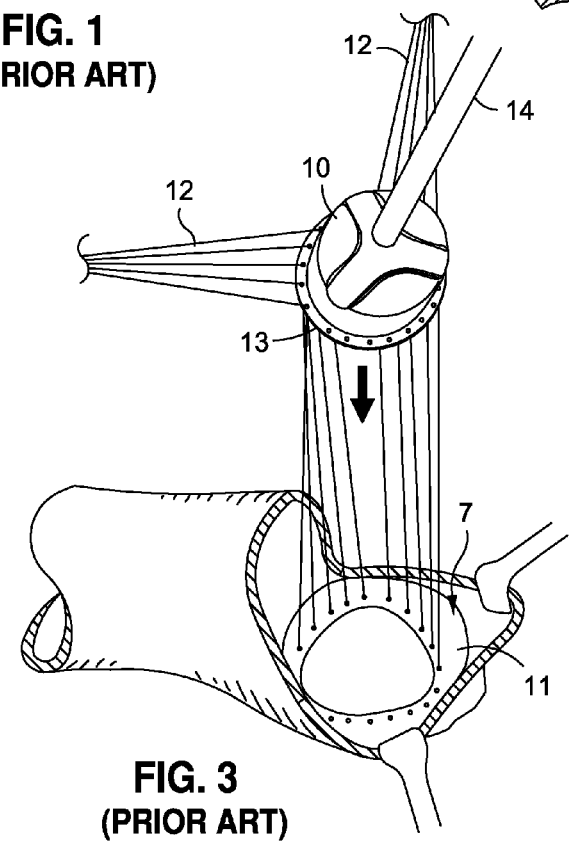
FIG. 1 (PRIOR ART)
FIG. 2 (PRIOR ART)
FIG. 3 (PRIOR ART)

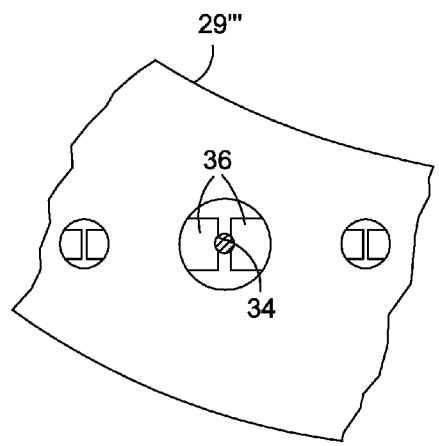 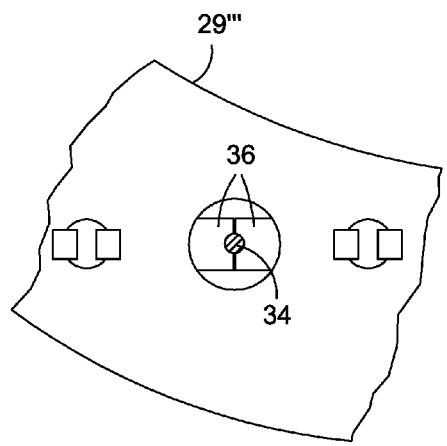
FIG. 15A  FIG. 15C
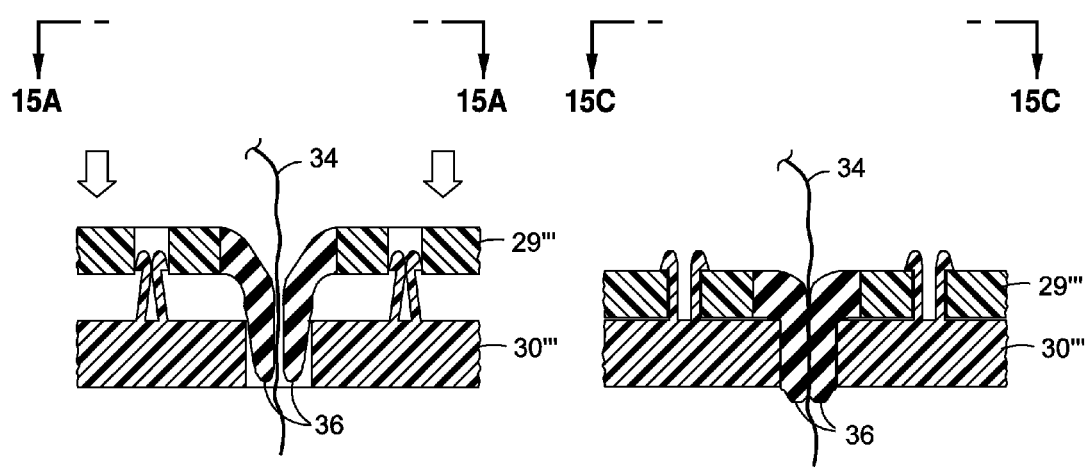
FIG. 15B  FIG. 15D

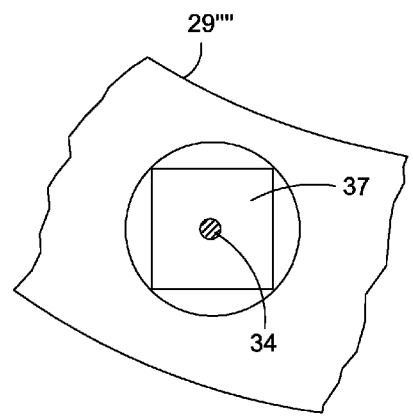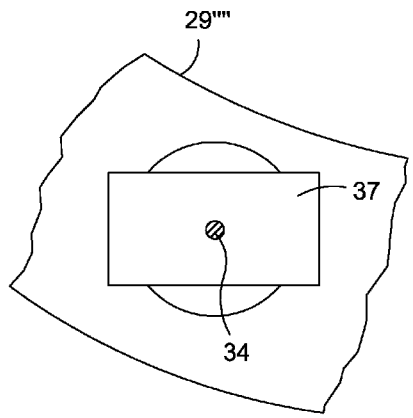
FIG. 16A        FIG. 16C
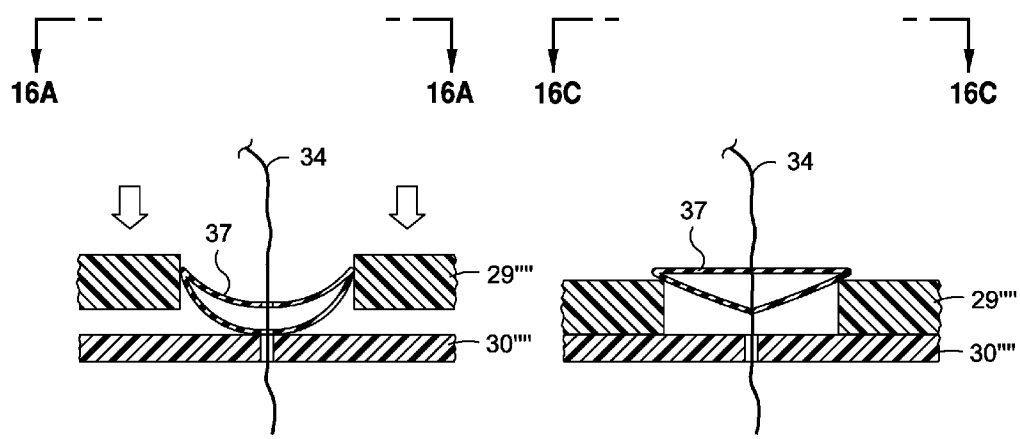
FIG. 16B        FIG. 16D

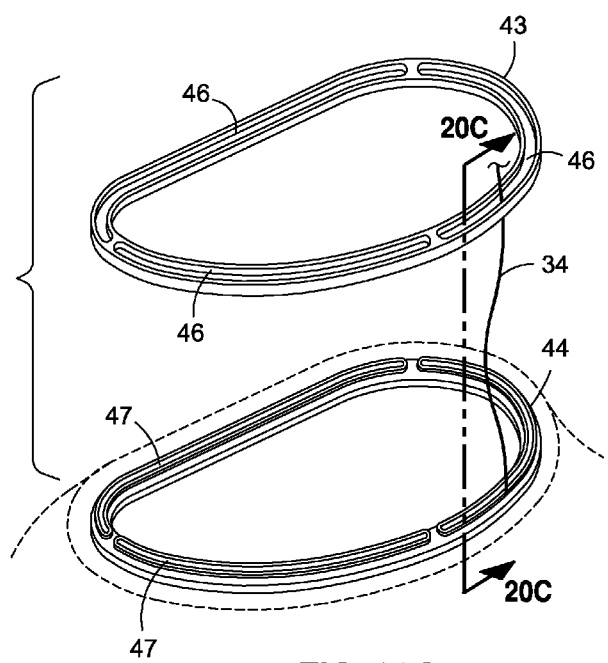
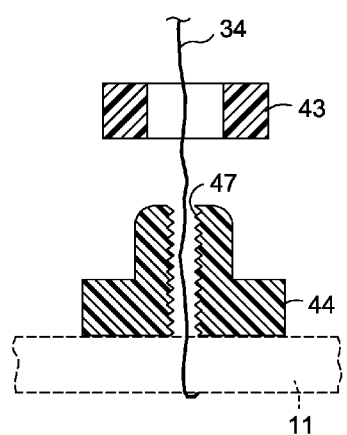
FIG. 20A
FIG. 20C
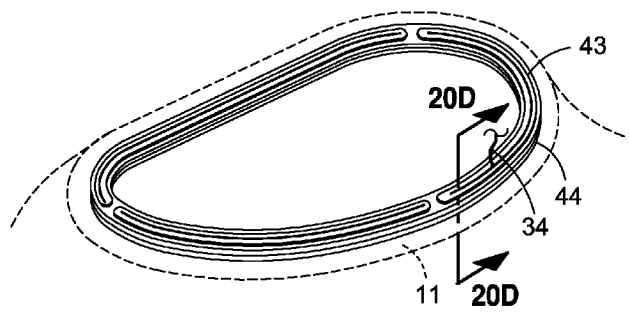
FIG. 20B
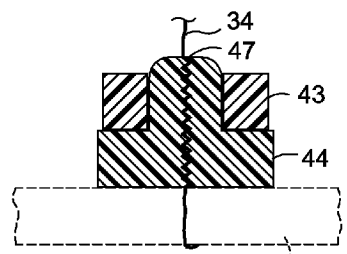
FIG. 20D

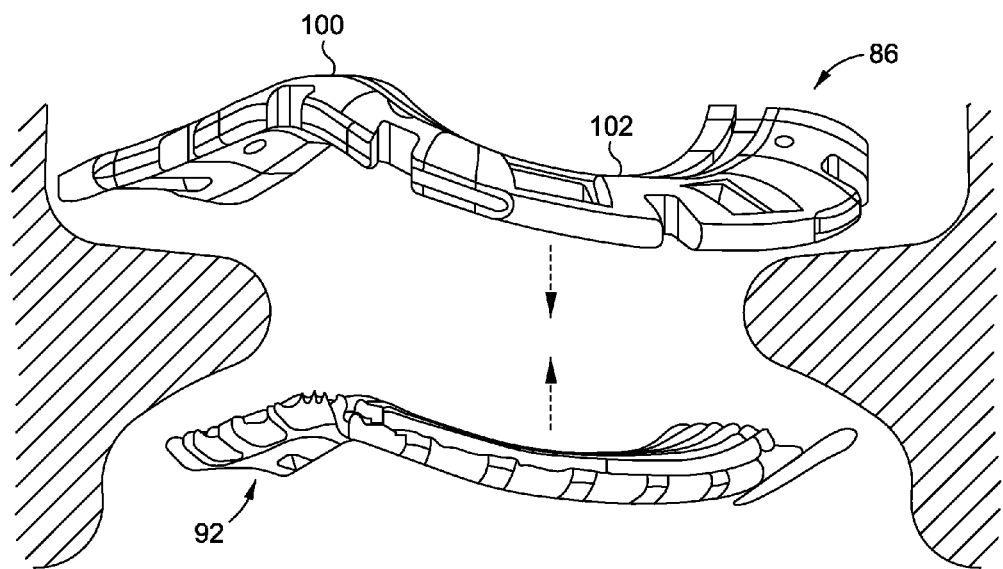
FIG. 25
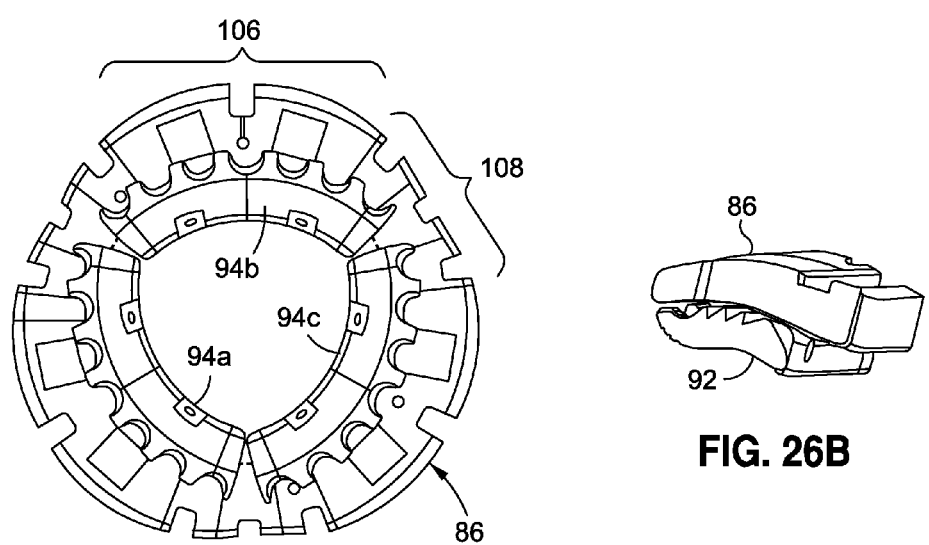
FIG. 26A
FIG. 26B

HEART VALVE PROSTHESIS ANCHORING DEVICE AND METHODS

RELATED APPLICATIONS

The present application claims priority under 35 U.S.C. §119 to U.S. Provisional Application No. 61/497,313, filed Jun. 15, 2011.

FIELD OF THE INVENTION

The present invention relates to heart valve surgery and more particularly to devices and methods for anchoring prostheses inside or near the heart.

BACKGROUND OF THE INVENTION

Many different surgical procedures benefit from anchors used to secure prostheses to tissue at various locations in the body. One area where this is true is in the field of heart valve repair. Heart valve repair is a procedure to fix or replace a damaged heart valve or tissue around the heart valve.

There are four main heart valves in the heart: the aortic, mitral, pulmonary, and tricuspid. The aortic valve is located at the outflow end of the left ventricle and empties into the aorta. The mitral valve is located at the outflow end of the left atrium and empties into the left ventricle. The pulmonary valve is located at the outflow end of the right ventricle and empties into the pulmonary artery. The tricuspid valve is located at the outflow end of the right atrium and empties in the right ventricle.

Stenosis is a common affliction that can negatively affect the function of a heart valve. Stenosis is when a heart valve becomes harder due to calcification that decreases the heart valve effectiveness. A typical treatment for a stenosed heart valve is heart valve replacement also known as valvuloplasty. One way a heart can be replaced is by cutting out the diseased valve and suturing a prosthetic valve in its place.

Another problem that can negatively affect the function of a heart valve is deformation of the heart valve annulus. A deformed heart valve annulus can reduce leaflet coaptation causing leakage, also known as regurgitation. Typically, clinicians use an annuloplasty ring to treat a deformed heart valve annulus. The annuloplasty ring can be sutured in place such that the annulus takes the shape of the annuloplasty ring. Both valvuloplasty and annuloplasty conventionally involve tying suture knots in order to secure a prosthesis in or near the heart.

Clinicians can perform traditional open heart surgery to repair a defective valve or can utilize a minimally invasive or transcatheter technique. Traditional open heart surgery involves administering anesthesia and putting a patient on cardio-pulmonary bypass. A clinician cuts open the chest to access the heart. Then the clinician cuts out the defective native valve leaflets leaving the annulus in place. The clinician places sutures in the annulus or other tissue near the heart valve. The free ends of the sutures are threaded through a sewing cuff on the heart valve prosthesis. The clinician "parachutes" the heart valve prosthesis into place by sliding it down the sutures until it rests on the annulus. To secure the prosthesis a clinician can tie each suture free end to another free end to prevent the sutures from backing out. This prevents the prosthesis from migrating away from the annulus. Normally, this process entails about 4-8 knots on each of the 12-20 sutures used per implant. Thus, the number of suture knots can be quite large.

What was just described was a procedure for implanting a prosthetic valve. To implant an annuloplasty ring a similar procedure is followed except that the native valve is typically left in place. The annuloplasty ring is sutured in place to reshape the valve annulus and improve native heart valve leaflet coaptation.

Minimally invasive and transcatheter techniques may also be used. Normally a collapsible surgical prosthesis is used with minimally invasive or transcatheter procedures. To implant the prosthesis using a minimally invasive technique, a clinician makes a small incision in the chest and uses special tools to pass the heart valve repair prosthesis through the incision. An example of a minimally invasive heart valve repair procedure is transapical aortic valve replacement. In a transcatheter technique, a clinician passes a catheter through a patient's vasculature to the desired location in the heart. Once there, the clinician deploys the surgical prosthesis and uses tools which can be passed through a patient's vasculature to secure the prosthesis in place. An example of a transcatheter heart valve repair procedure is transfemoral aortic valve replacement.

Within the prior art there exists a need for devices and methods that reduce the time required to secure a heart valve repair prosthesis in place. Currently a clinician must tie a multitude of knots in sutures which can take a great deal of time. This lengthens the time a patient is on cardio-pulmonary bypass and under anesthesia. Thus, any reduction in surgical time that a patient undergoes would be beneficial.

Additionally, there exists a need to make it easier to secure a heart valve repair prosthesis in place. Currently, a clinician must work in the limited space near the heart to tie knots in sutures. This is a cumbersome process that benefits from a clinician of great dexterity and patience. In a minimally invasive or transcatheter surgery, the clinician must use tools that can be passed through a small incision, thus making the tying of knots even more difficult. Therefore, any improvement in ease of use would be beneficial.

Further still, there exists a need to increase the robustness of the attachment of a heart valve repair prosthesis. In order for the prosthesis to achieve maximum effectiveness, it must be coupled to the tissue around the heart valve and form a tight seal. For example, in the case of a prosthetic heart valve, the sewing ring must seal against the heart valve annulus such that no blood leaks around the outside of the sewing ring. Any leaks would decrease the effectiveness of the prosthetic valve. Thus, an increase in the robustness of the bond formed between the heart valve repair prosthesis and the annulus would be beneficial.

SUMMARY OF THE INVENTION

The present invention provides new apparatus and methods for securing heart valve repair or replacement prostheses in or near the heart. The apparatus and methods are particularly well suited for traditional surgery or minimally invasive surgery. The invention reduces the number of surgical knots thus reducing surgical time and exposure. The invention improves the ease of implantation because it reduces or eliminates the surgical knots a clinician would normally tie in the limited space in and around the heart. Additionally, embodiments of the invention provide a more robust attachment for heart valve repair or replacement prostheses.

In accordance with one exemplary embodiment, a knotless heart valve prosthesis includes a lower segmented ring having an implanted size that can be collapsed to a smaller size for passage through an annulus. An upper securing ring connects to a prosthetic heart valve. A plurality of elongated flexible connection members extend upward from the segmented ring through mating apertures formed in the securing ring so as to couple the two rings together and clamp a valve annulus therebetween, thereby securing the heart valve to the valve annulus without sutures. The prosthesis may further have a plurality of protruding members that extend generally radially outward from the lower segmented ring that help anchor the heart valve to the valve annulus. Desirably, the lower segmented ring includes rows of teeth on an upper surface thereof that help anchor the heart valve to the valve annulus.

In a preferred embodiment, the lower segmented ring comprises three separate segments arranged in a circumferential array with gaps therebetween. Further, flexible links may join the three separate segments of the lower segmented ring. The connection members may comprise elongate strips with ratcheting teeth, and the apertures in the securing ring include ratchet pawls that engage the ratchet teeth on the connection members. Alternatively, the connection members comprise sutures, and the mating apertures in the securing ring comprise suture clamps. Preferably, the securing ring has an undulating contour with three axially elevated peaks intermediate three axial valleys, and wherein the lower segmented ring generally mimics the undulating contour of the securing ring and has three segments that correspond to the three axially valleys of the securing ring, and wherein there are at least two connection members extending upward from each segment of the lower segmented ring.

In accordance with another preferred embodiment, a knotless aortic heart valve prosthesis comprises a prosthetic heart valve having a securing ring extending outward from an inflow end thereof. The securing ring has an undulating contour with three outwardly projecting lobes intermediate three radially inward relief areas, the relief areas defining axial peaks and the lobes defining axial valleys, and the securing ring having apertures therethrough. A lower segmented ring smaller in circumference than the securing ring and having an undulating shape mimics the shape of the securing ring. Finally, a plurality of elongated flexible connection members extend upward from the segmented ring through the apertures formed in the securing ring so as to couple the two rings together and clamp a valve annulus therebetween, thereby securing the heart valve to the valve annulus without sutures. The prosthesis may further have a plurality of protruding members that extend generally radially outward from the lower segmented ring that help anchor the heart valve to the valve annulus. Desirably, the lower segmented ring includes rows of teeth on an upper surface thereof that help anchor the heart valve to the valve annulus.

In another preferred embodiment, the lower segmented ring comprises three separate segments arranged in a circumferential array with gaps therebetween. Further, flexible links may join the three separate segments of the lower segmented ring. The connection members may comprise elongate strips with ratcheting teeth, and the apertures in the securing ring include ratchet pawls that engage the ratchet teeth on the connection members. Alternatively, the connection members comprise sutures, and the mating apertures in the securing ring comprise suture clamps.

A method for implanting an aortic heart valve prosthesis comprises the steps of
  a. inserting a segmented lower ring downward through an aortic annulus from the atrial to ventricular side, the lower ring having three segments that may be arranged together below the aortic annulus in a non-circular ring shape, each segment having at least one connection member secure thereto and projecting upward through the aortic annulus to the atrial side thereof;
  b. advancing a heart valve and securing ring toward the aortic annulus, the securing ring extending outward from an inflow end of the heart valve and having apertures therethrough;
  c. inserting each of the connection members extending upward from the lower ring through an aperture in the securing ring around the heart valve;
  d. advancing the heart valve and securing ring into contact with the aortic annulus;
  e. applying tension to the connection members so as to clamp the aortic annulus between the lower ring and the securing ring;
  f. securing the position of each connection member within its respective aperture; and
  g. trimming each connection member closely above its respective aperture.

Preferably, the three segments of the lower ring are joined by flexible links. Additionally, the securing ring may have an undulating contour with axial peaks intermediate axial valleys, and a non-circular periphery with outwardly projecting lobes coinciding with the axial valleys and radially inward relief areas coinciding with the axial peaks. Furthermore, the three segments of the segmented lower ring preferably coincide with the outwardly projecting lobes of the securing ring, and have gaps therebetween coinciding with the radially inward relief areas of the securing ring. The connection members may comprise elongate strips with ratcheting teeth, and the apertures in the securing ring include ratchet pawls that engage the ratchet teeth on the connection members, and wherein the step of securing the position of each connection member within its respective aperture occurs by applying tension to the connection member.

In another embodiment, the invention is an implantable prosthesis anchor comprising: an upper support section; a lower support section; and at least one tension member; wherein the tension member is configured to apply forces to the upper support section and the lower support section such that the upper support section engages one surface of a heart annulus while the lower support section engages an opposing surface of the heart annulus.

In one instance, the tension member is a length of suture material that passes through the upper support section and the lower support section in an alternating fashion forming a zigzag pattern around the periphery of the implantable prosthesis anchor. In another instance, each tension member comprises a strip with ratchet teeth, the upper support section further comprises at least one tension member receiver, each tension member receiver comprises a pawl, and wherein the upper support section is configured to ratchet towards the lower support section by way of the pawl on each tension member receiver engaging the ratchet teeth of each tension member. In yet another instance, no tension member passes through native tissue. In yet another instance, the upper support section further comprises barbs adapted to contact annulus tissue that aid in clamping a portion of the heart annulus and the lower support section further comprises barbs adapted to contact annulus tissue that aid in clamping a portion of the heart annulus.

In one instance, the upper support section and the lower support section are made of a flexible material to allow either the upper support section or the lower support section to be elastically deformed and passed through the annulus of the heart. In another instance, the upper support section and the lower support section are collapsible down to a size suitable for trans-catheter delivery. In yet another instance, the upper support section and the lower support section are of a scalloped shape to better fit in a heart valve annulus. In yet another instance, the invention can further comprise a prosthetic heart valve attached to the upper support section. In yet another instance, the invention can further comprise a tubular cloth portion comprising a first end and a second end, wherein the cloth portion is attached at the first end to the upper support section and attached at a second end to the lower support section.

In another embodiment, the invention can be an implantable prosthesis anchor comprising: a lower support section with a plurality of engaging hooks extending off of an upper portion of the lower support section; an upper support section with a plurality of receiving holes; and a length of suture material passed through native tissue at least once and passed through the lower support section at least once; wherein the engaging hooks of the lower support section are configured to mate into the receiving holes of the lower support section and the length of suture material is configured to become clamped to the anchor when the upper support section is mated to the lower support section.

In one instance, the upper support section and the lower support section are collapsible down to a size suitable for trans-catheter delivery. In another instance, the invention can further comprise a plurality of locking members disposed within the prosthesis anchor to aid in clamping the length of suture material. In yet another instance, the locking members consist of pairs of flexible tubular members located in the suture holes that are configured to clamp the suture material when the upper support section mates into the lower support section. In yet another instance, the locking members consist of hinged flaps located in the suture holes that are configured to clamp the suture material when the upper support section mates into the lower support section. In yet another instance, the upper support section and the lower support section are configured to form an annuloplasty ring when mated together.

In yet another embodiment, the invention can be a method for implanting a prosthesis comprising the steps of: providing a prosthesis anchor comprising an upper support section, a lower support section, and a tension member; deploying the upper support section in the heart of a human patient; deploying the lower support section adjacent to the upper support section; applying a force to the tension member to draw the upper support section and lower support section towards each other causing native tissue to become clamped between the upper support section and the lower support section; and securing the tension member to fix the prosthesis anchor in place within the heart.

In one instance, the tension members comprise strips with ratchet teeth. In another instance, the invention can further comprise the step of attaching the lower support section to native heart tissue with at least one length of suture material. In yet another instance, the invention can further comprise the step of securing a heart valve to the upper support section.

In accordance with a further aspect of the application, an implantable prosthesis anchor and heart valve combination comprises an annulus anchor having a resilient upper ring and a resilient lower ring, and an annular connection portion therebetween, the annular connection portion having a smaller diameter to match a target annulus. The anchor is deployable to the target annulus so that the upper and lower rings flank the target annulus and the connection portion spans the target annulus. A prosthetic heart valve has an annular mating portion along its outside surface that clips onto the upper and lower rings of the annulus anchor. The annular connection portion preferably comprises one or more sutures that thread through sleeves located at spaced apart locations on the upper and lower rings, wherein the one or more sutures may be tensioned to pull the upper and lower rings toward each other and clamp against the target annulus. In one embodiment, the annular connection portion comprises a cloth surface with no gaps that covers the target annulus. In another embodiment, the annular connection portion comprises one or more resilient spring members biased to pull the upper and lower rings toward each other and clamp against the target annulus.

A further aspect of the present application includes an implantable prosthesis anchor that has a first support ring with a plurality of protruding members extending off of a facing surface. A second support ring having a plurality of receptacles in a facing surface that is sized to receive the protruding members on the first support ring. The facing surfaces of the first and second support rings may be brought together so that the protruding members of the first support ring are received into the receptacles of the second support ring. A plurality of lengths of suture material pass through native tissue at least once and each pass through one of the receptacles of the second support section. When the first support section mates to the second support section the protruding members each clamp a length of suture against the receptacle. In one version, implantable prosthesis anchor includes a prosthetic heart valve attached to one of the first and second support rings. Alternatively, one of the first and second support rings comprises an annuloplasty ring. In alternate embodiments, the protruding members and receptacles each comprise a cleat-style suture clamp or a button-style suture clamp.

Another implantable prosthesis anchor disclosed herein includes a first support ring with a plurality of receptacles in a facing surface, and a second support ring with a plurality of receptacles in a facing surface, wherein the facing surfaces of the first and second support rings may be brought together so that corresponding receptacles align. The prosthesis anchor further has a plurality of clips protruding from the facing surface of one of the first and second support rings and a plurality of mating opening in the other of the first and second support rings, the clips and openings holding the first and second support rings together. Furthermore, a plurality of compressible members are sized to fit between the aligned receptacles in the first and second support rings, the corresponding receptacles having a mutual size so as to compress the compressible members. A plurality of lengths of suture material passed through native tissue at least once and each pass through a pair of corresponding receptacles, wherein the compressible members each clamp a length of suture when the first support section mates to the second support section and engages the mating clips and openings. The compressible members desirably comprise elements separate from either of the first and second support rings. For instance, the compressible members comprise springs, or flaps extending from one of the first and second support rings.

Another implantable prosthesis anchor and heart valve combination disclosed herein includes a first support ring with a plurality of protruding members extending off of a facing surface, and a second support ring with a plurality of protruding members extending off of a facing surface. A prosthetic heart valve connects to the second support ring, and a plurality of elongated ratchet members extend from the first support ring through mating apertures formed in the second support ring so as to couple the two rings together.

An exemplary method for implanting a prosthesis disclosed herein comprises the steps of:
 a. providing a prosthetic heart valve having a soft flange;
 b. providing a plurality of elongated hook members distributed around the soft flange, the hook members each having a curved distal end with a sharp tip;

c. advancing the assembly of the heart valve and hook members into an implant position with the soft flange on the outflow side of a heart valve annulus and the curved distal ends on the inflow side;

d. pulling the hook members proximally through the soft flange so that the curved distal ends engage an underside of the annulus and the sharp tips pierce the annulus tissue to embed the hook members therein; and e. securing the soft flange to the hook members.

Disclosed herein are devices and methods for quickly, easily, and conveniently affixing a heart valve repair prosthesis to tissue within or near the heart. The invention advantageously reduces or eliminates the need to manually tie suture knots, a procedure that often entails the difficult process of manipulating sutures in the tight space around the surgery site. The invention can provide these advantages in any procedure where surgical knots are needed, especially where access may be limited, such as for example, in a minimally invasive or transcatheter procedure.

Disclosed herein are devices and methods that limit the physical exposure and time required in surgical knot tying. The invention advantageously allows for enhanced securing to tissue with minimal surgical exposure, implantation time and improved reliability. This can reduce the cost of surgery and increase the efficient use of clinicians' time. Additionally, the knotless embodiments of the present invention eliminate suture tails that can cause abrasion in the surrounding tissue. The present invention can lead to shortened hospital stays and a lower rate of repeat surgical interventions to correct complications.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 1 is a drawing of a prior art heart valve implanted in the aortic valve position of a human heart.

FIG. 2 is an enlarged view of the prior art heart valve of FIG. 1.

FIG. 3 is a drawing of an intermediate step of the implantation procedure of the prior art heart valve shown in FIG. 1.

FIGS. 15A-D are multiple views of yet another alternative compressive attachment portion of an anchoring device according to an alternative embodiment of the present invention.

FIGS. 16A-D are multiple views of yet another alternative anchoring device according to an alternative embodiment of the present invention.

FIGS. 20A-D are multiple views of an annuloplasty device according to yet another embodiment of the present invention.

FIGS. 23-26 illustrate a further alternative knotless heart valve anchoring system that uses shaped flanges connected by cable ties.

DETAILED DESCRIPTION OF THE PREFERRED EMBODIMENTS

Figure 4:
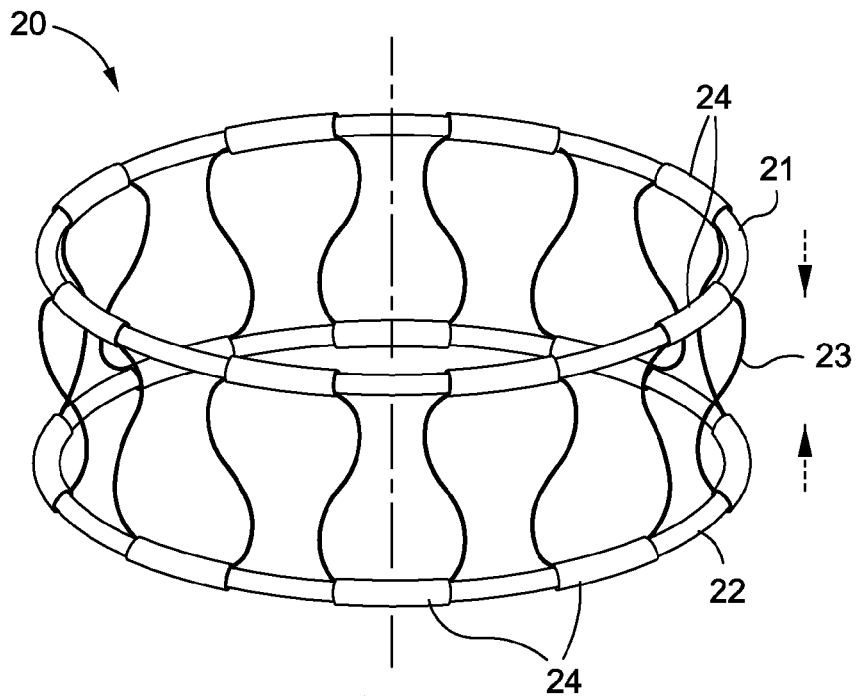
FIG. 4 is a drawing of a dual-ring annulus anchoring device with a filamentary connection portion according to one embodiment of the present invention.

Various embodiments of the present invention comprise heart valve repair or replacement prosthesis anchors that are well-suited for improving ease of implantation, reducing surgical exposure, and improving prosthesis attachment. It should be appreciated that the principles and aspects of the embodiments disclosed and discussed are also applicable to other devices having different structures and functionalities. For example, certain structures and methods disclosed may be applicable to other types of surgical procedures, namely annuloplasty ring implant for heart valve repair. Furthermore, certain embodiments may also be used in conjunction with other medical devices or other procedures not explicitly disclosed. However, the manner of adapting the embodiments described to various other devices and functionalities will become apparent to those of skill in the art in view of the description that follows.

A schematic drawing of a prior art prosthetic heart valve implanted in the heart 1 is shown in FIG. 1. The left atrium 2 and the left ventricle 3 are shown separated by the mitral valve 6. The aortic valve 7 is at the outflow end of the left ventricle 3. On the opposite side of the heart, the right atrium 5 and the right ventricle 4 are shown separated by the tricuspid valve 8. The pulmonary valve 9 is at the outflow end of the right ventricle 4. A prior art prosthetic heart valve 10 is shown implanted in the aortic valve 7 position.

An enlarged view of the aortic valve 7 is shown in FIG. 2. The aortic annulus 11, a fibrous ring extending inward, can be seen with the prior art prosthetic heart valve 10 sutured in place above it. A step of the procedure to implant the prior art prosthetic heart valve 10 is shown in FIG. 3. During implantation, a clinician passes sutures 12 through the annulus 11 of the aortic valve 7. While the heart valve is held on a fixture or holder 14, a clinician can thread the suture 12 free ends through a sewing ring 13 on the prosthetic heart valve 10. Thus, both free ends of each suture 12 extend out of adjacent portions of the sewing ring 13. The valve 10 is then 'parachuted' down in the direction shown. The clinician moves the valve 10 down the array of sutures 12 and pulls the sutures 12 tight so that a seal is formed between the sewing ring 13 and the aortic annulus 11. Next, the clinician ties each suture 12 free end to another free end securing the prosthetic heart valve 10 in place. Normally this process entails about 4-8 knots per suture and 12-20 sutures are used per implant. The ends of each suture 12 are clipped leaving a suture tail comprised of the suture used to create each knot.

Turning now to the present invention, certain efficiencies which reduce the procedure time will be explained. In the description that follows, the aortic annulus is used as the implantation site to illustrate the embodiments. The teachings of this invention can also be applied to the mitral, pulmonary, and tricuspid valves; or indeed, other valves in the body, including venous valves. Where possible, variations of each embodiment are discussed serially with common numbers used for common structure. Where structure is similar but design varies from device to device, each new instance of structure is given a prime symbol to denote its difference from a prior version. For, example 22, 22', and 22" refer to three different designs for a similar part of several embodiments.

An anchoring device 20 according to one embodiment of the present invention is shown in FIG. 4. The device comprises an upper ring 21, a lower ring 22 and a resilient connection portion 23 that tends to bring the upper and lower rings together. In a preferred embodiment the upper ring 21 and lower ring 22 are made out of a flexible biocompatible metal such as stainless steel. The connection portion 23 can consist of a flexible elongate material such as one or more lengths of metal thread or wire. In a preferred embodiment, the connection portion 23 comprises suture material made of a synthetic polymeric fiber. In one embodiment, a single length of suture material of the connection portion 23 passes in and out of sleeves 24 located at spaced apart locations on the upper and lower rings. Alternatively, the connection portion 23 can comprise one or more stiff members such as rods to bring the upper and lower ring together and clamp onto tissue. In general, the connection portion 23 either acts like a plurality of tension springs that bias the upper and lower rings toward one another, or if it is a length of suture material it can be cinched to pull the rings together.

Figure 5:
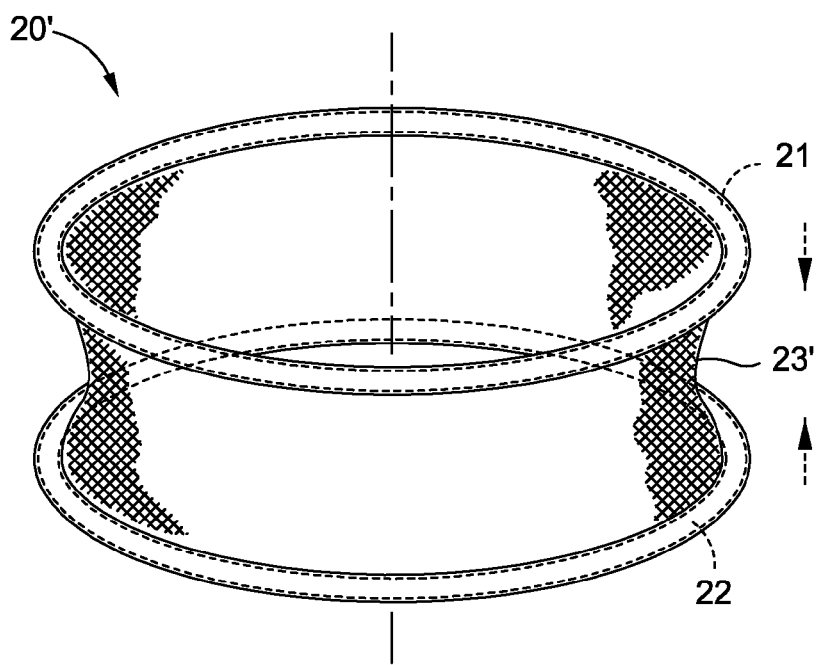
FIG. 5 is a drawing of an alternative dual-ring annulus anchoring device with a cloth connection portion according to another embodiment of the present invention.

An alternative device according to one embodiment of the present invention is shown in FIG. 5. The device 20' is similar to the device 20 in that it has an upper ring 21 and a lower ring 22. But the alternative device has a connection portion 23' that is comprised of a section of cloth. The cloth preferably is a synthetic biocompatible type cloth such as polytetrafluoroethylene (e.g. Teflon PTFE) or polyester (e.g. Dacron), although other synthetic or natural cloths may be used.

Figure 6:
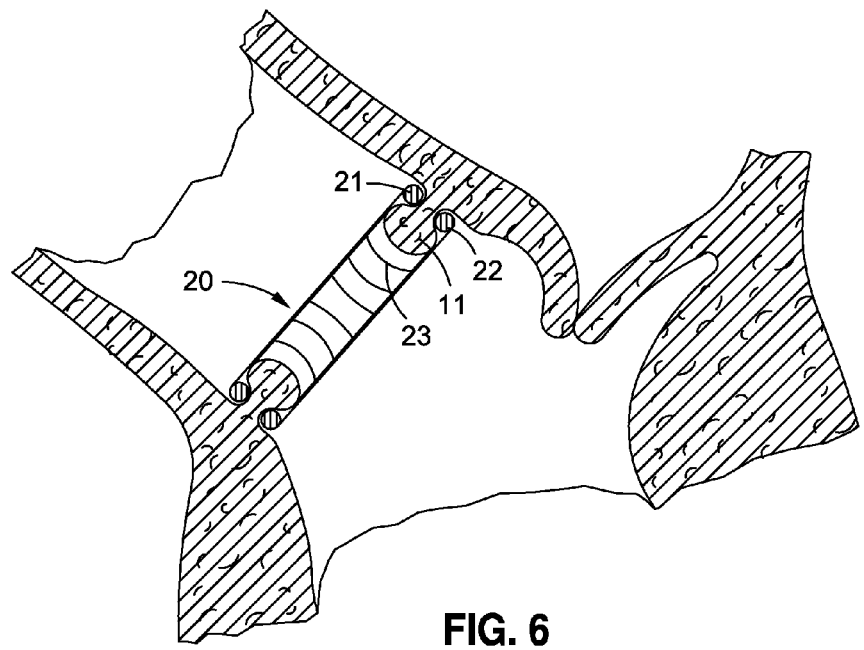
FIG. 6 is a drawing of the anchoring device of FIG. 4 implanted near an annulus of the human heart.

Turning back to the anchor 20 shown in FIG. 4, preferably the anchor 20 is flexible such that it can be deformed and passed through an annulus of a heart valve. This can be accomplished by a clinician in a traditional open heart surgery or via tools used in a minimally invasive or transcatheter procedure. The anchor 20 is shown in a deployed state in FIG. 6. The resilient upper ring 21 is located above the annulus 11, while the resilient lower ring 22 is located below the annulus 11. The anchor 20 is deployable to the target annulus so that the upper and lower rings 21, 22 expand to flank the target annulus and the connection portion 23 which has a smaller diameter spans the target annulus. The connection portion 23 pulls the upper ring 21 towards the lower ring 22. In a preferred embodiment, the connection portion 23 is a length of suture material that can be tensioned by pulling on a free exposed end. This allows a clinician to tighten the anchor 20 onto the annulus 11 and clamp tissue in between the upper ring 21 and the lower ring 22. In addition, the open areas between the suture material in the connection portion 23 will allow tissue to protrude through and become trapped in between. The protruding tissue aids in securing the device and promotes tissue ingrowth. The suture can be secured by crimping the sleeve 24 adjacent the free end of the suture. Alternatively, the suture free end may be tied to another free end or to another location on the anchor 20.

With respect to the alternative device in FIG. 5, the connection portion 23' is comprised of a section of cloth and thus does not bias the rings 21, 22 together. However, the diameter of the rings is greater than that of the valve annulus and thus one of the two rings can be compressed to pass through the annulus whereupon the two rings expand outward on either side to flank the annulus (as in FIG. 6). The cloth connection portion 23' circumscribes and covers the native annulus, thus evening out irregularities and containing loose pieces of calcification and the like.

Figure 7:
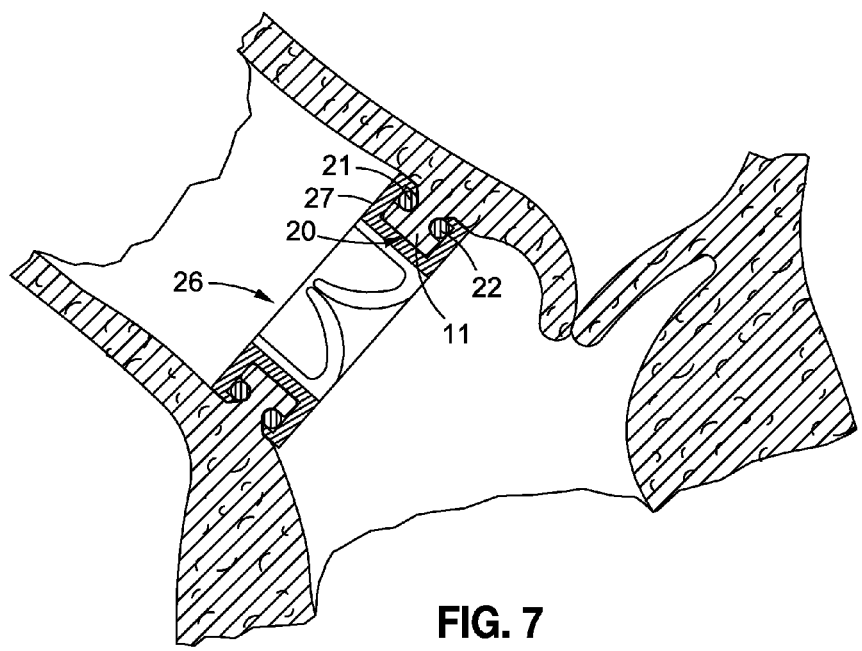
FIG. 7 is a drawing of a prosthetic heart valve installed over the anchoring device shown in FIG. 4.

A heart valve 26 is shown deployed over the anchor 20 in FIG. 7. The heart valve 26 has an annular mating portion 27 along its outside surface that clips onto the upper and lower rings 21 and 22 of the anchor 20. The mating portion 27 of the heart valve also applies pressure to the annulus 11 to ensure a robust and leak free fit.

Figure 8:
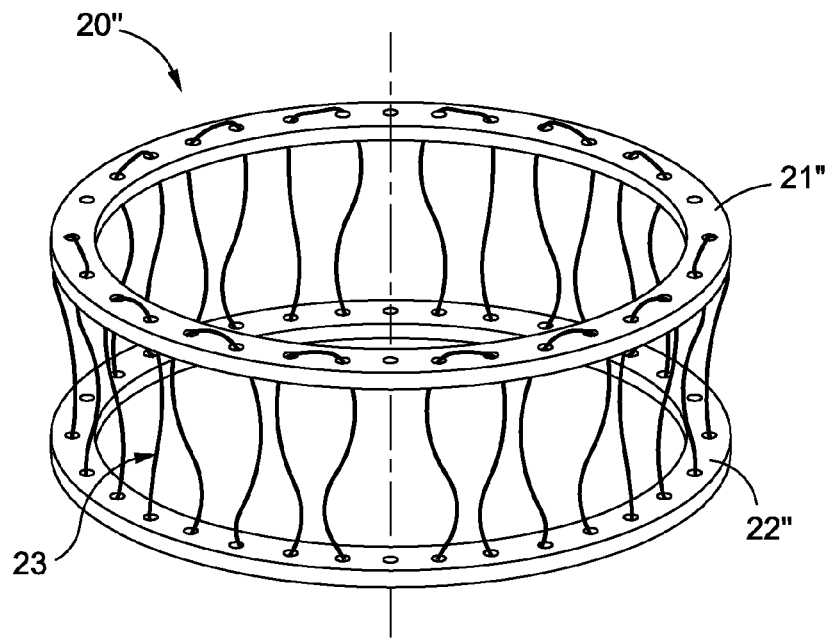
FIG. 8 is a drawing of an alternative dual-ring annulus anchoring device according to one embodiment of the present invention.
Figure 9:
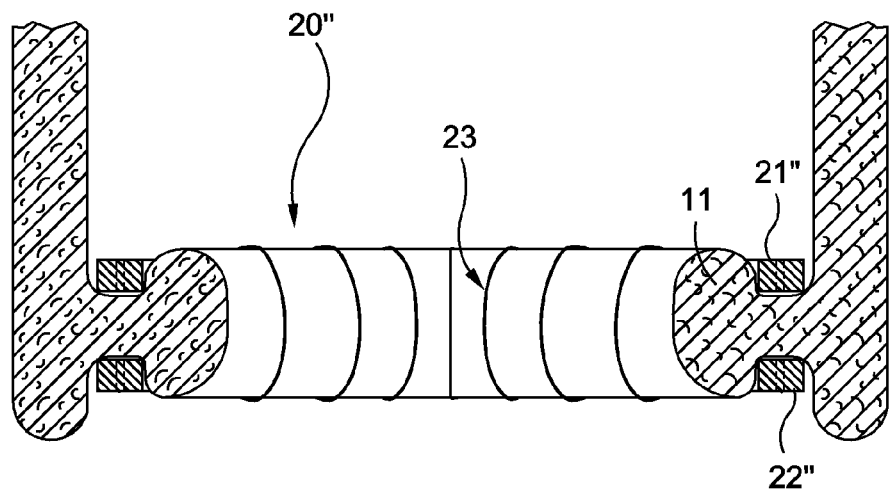
FIG. 9 is a drawing of the anchoring device shown in FIG. 8 implanted in an annulus of the human heart

An alternative anchor 20" is shown in FIG. 8. This device is similar to the anchor 20 shown in FIG. 4 except that the upper ring 21" and lower ring 22" are flat rings with a plurality of holes. Preferably, one or both of the rings 21", 22" are made of a flexible polymeric material so that a clinician may bend one of the rings and pass it through the native annulus during implantation. Alternatively, the upper ring 21" and lower ring 22" may be made of a rigid material, and the anchor can be tilted and passed through the annulus sideways, using the natural elasticity of the annulus to accommodate insertion. A suture, 23 loops through the holes in ring in an alternating fashion to join the upper ring 21" and lower ring 22". The anchor 20" is shown in an implanted state in FIG. 9. The design of the anchor 20" allows it to be clamped onto the annulus like the device 20 in FIG. 4. A clinician can pull on a free end of the suture 23 to draw the upper ring 21" toward the lower ring 22". The suture can then be secured with a single knot to fix the anchor in place.

Figure 10:
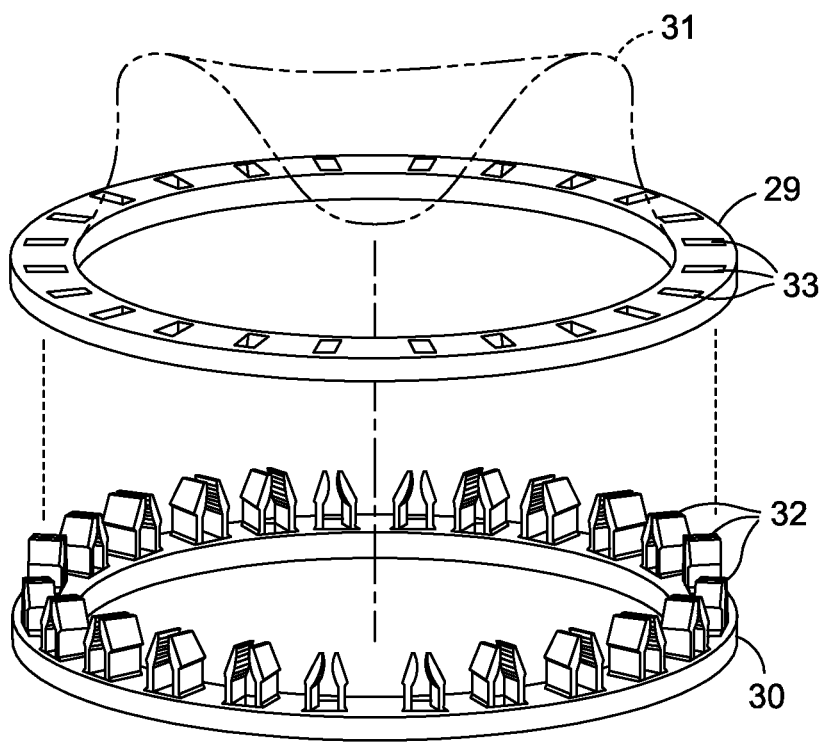
FIG. 10 is a drawing of a dual-ring annulus anchoring device having cleat-style attachment clips according to another embodiment of the present invention.
Figure 11:
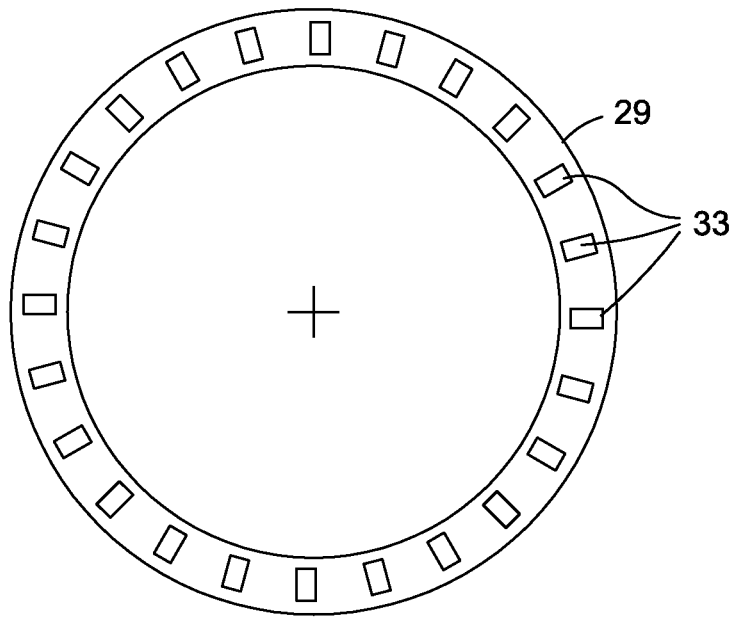
FIG. 11 is a top view of the anchoring device of FIG. 10.

A device according to an alternative embodiment of the present invention is shown in FIG. 10. This device is a two-part anchor for a heart valve repair prosthesis. The bottom portion comprises a sewing ring 30 and the top portion comprises a locking ring 29. Preferably, the sewing ring 30 and the locking ring 29 are made of a semi-rigid polymeric material. A heart valve 31 may be attached to the locking ring 29 as shown in FIG. 10. Alternatively, the device may be used as an annuloplasty ring without a heart valve attached to the locking ring 29. The sewing ring 30 comprises cleat-style clips 32 that mate into holes 33 on the locking ring 29. FIG. 11 shows a top view of the locking ring 29 and holes 33.

Figure 12A:
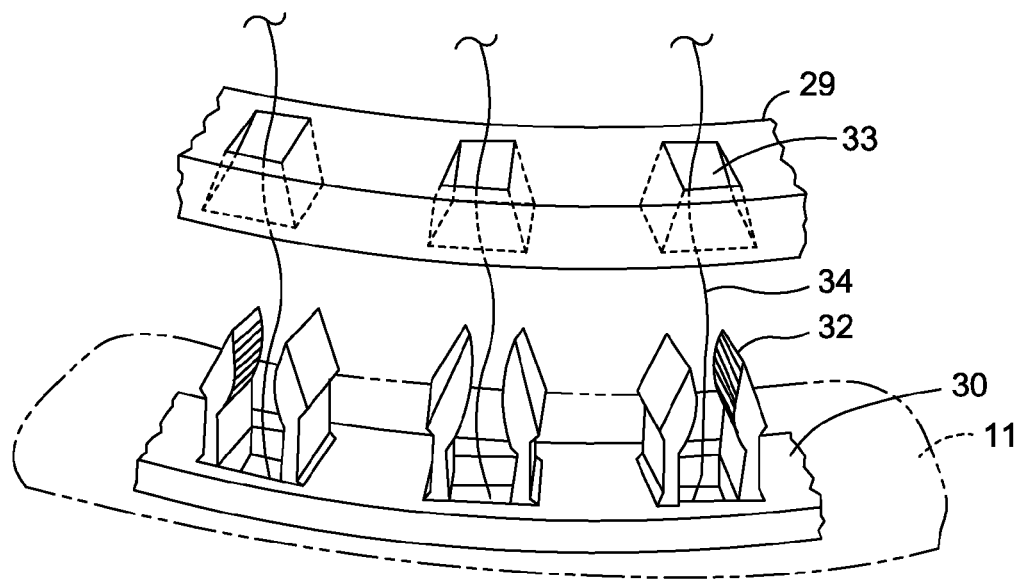
FIGS. 12A-B are enlarged views of the attachment portion of the anchoring device of FIG. 10.
Figure 12B:
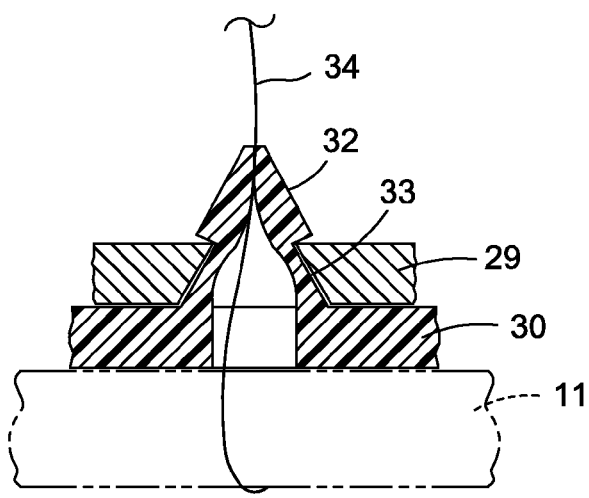

A close-up view of the clips 32 on the sewing ring 30 in an unlocked state is shown in FIG. 12A. To implant the anchor, a clinician places at least one suture 34, and typically an array of sutures, through the tissue of the annulus 11. A clinician can place the free ends of each suture through the hole between the clips 32 on the sewing ring 30. Preferably, the two free ends of each suture will be placed through adjacent clips 32 on the sewing ring 30. Once all sutures 34 have been placed, the clinician presses the locking ring 29 down on the sewing ring 30 transforming the device into a locked state as shown in FIG. 12B. The holes 33 in the locking ring 29 are tapered to force each of the two arms of the clips 32 on the sewing ring 30 towards each other to secure the suture 34 in between. This prevents each suture 34 from backing out and secures the device to the annulus 11. Also, the inner facing surfaces of each clip 32 finger are desirably roughened, grooved, have teeth or otherwise have a characteristic that enhances their grip onto the sutures. The illustrated embodiment acts like a cam cleat on a sailboat which tightens on the line in tension.

Figure 13A:
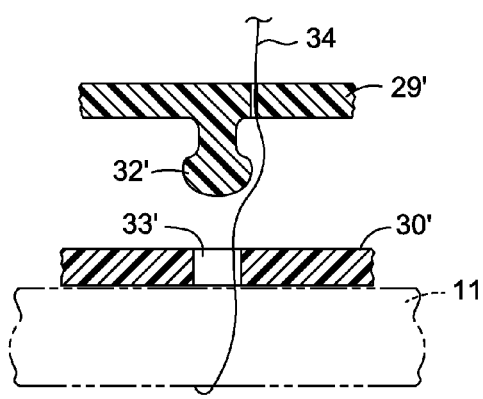
FIGS. 13A-B are section views of an alternate button-style attachment portion of an anchoring device according to an alternative embodiment of the present invention.
Figure 13B:
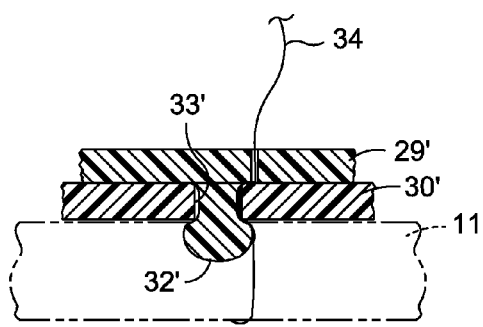

An alternative button-style suture fastening design is show in FIGS. 13A-B. In this design, the sewing ring 30' has holes 33' that mate with buttons or tabs 32' on the locking ring 29'. The device is shown in an unlocked state in FIG. 13A. Each suture 34 free end that has been pre-installed at the annulus passes through a hole 33' on the sewing ring 30' and then through a hole in the locking ring 29' that is near an associated tab 32'. When a clinician pushes the locking ring 29' down onto the sewing ring 30' the device transforms to a locked state as shown in FIG. 13B. In the locked state, the suture 34 free end is secured between the side of the tab 32' and the hole 33'. This prevents each suture 34 from backing out and secures the device to the annulus 11.

Figure 14A:
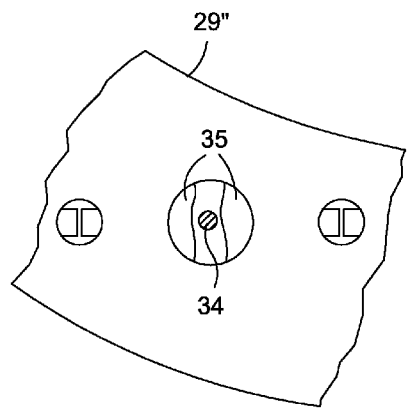
FIGS. 14A-D are multiple views of another alternative compressive attachment portion of an anchoring device according to an alternative embodiment of the present invention.
Figure 14C:
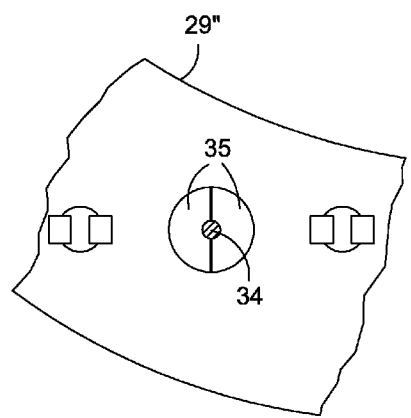
Figure 14B:
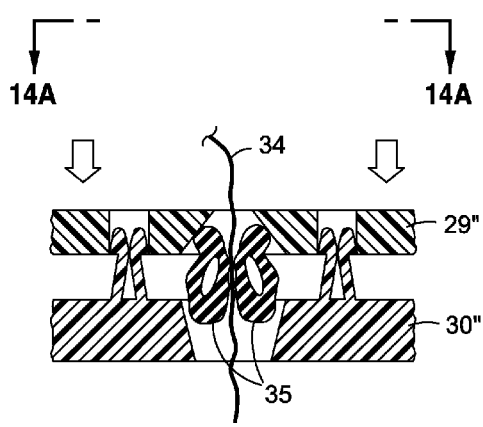
Figure 14D:
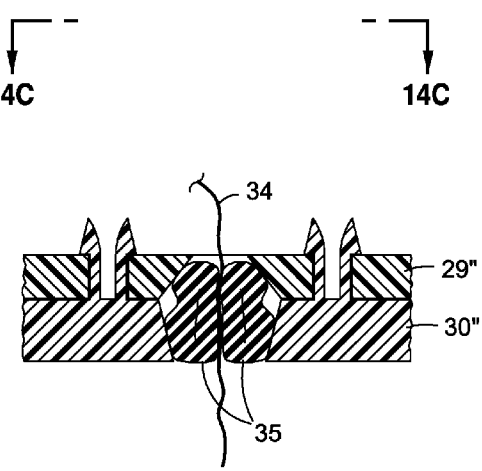

Another alternative suture fastening design is shown in FIGS. 14A-D. A device according to this design further comprises compressible suture gripping elements 35 disposed within a cavity created by holes in the locking ring 29" and the sewing ring 30". Preferably, the suture gripping elements are a pair of flexible generally tubular elastomeric (e.g., silicone) members. The device is shown in an unlocked state in FIGS. 14A-B. Each suture 34 free end that has been pre-installed at the annulus passes between the suture gripping elements 35. When a clinician pushes the locking ring 29" down on the sewing ring 30" the device transforms into a locked state as shown in FIGS. 14C-D, with a plurality of clips (not numbered) protruding from the facing surface of the sewing ring 30" extending into mating openings in the locking ring 29" to hold the two rings together. The tapered walls of the cavity formed between the locking ring 29" and the sewing ring 30" force the suture gripping elements 35 towards each other gripping each suture 34 free end. This prevents each suture 34 from backing out and secures the device to the annulus 11.

Yet another alternative device fastening design is shown in FIGS. 15A-D. A device according to this design further comprises resilient hinged flaps 36 attached to the locking ring 29''' and extending down through holes in the sewing ring 30'''. Preferably, the hinged flaps 36 are made from a flexible polymeric material. The device is shown in an unlocked state in FIGS. 15A-B. Each suture 34 free end that has been pre-installed at the annulus passes between the hinged flaps 36. When a clinician pushes the locking ring 29''' down on the sewing ring 30''' the hinged flaps 36 are compressed inward to retain the sutures 34 and transform the device into a locked state as shown in FIGS. 15C-D. Again, clips and mating openings (not numbered) hold the two rings together. The walls of each hole in the sewing ring 30''' force the hinged flaps 36 towards each other and grip the each suture 34 free end. This prevents each suture 34 from backing out and secures the device to the annulus 11.

Yet another alternative suture fastening design is shown in FIGS. 16A-D. A device according to this design further comprises spring clips 37 disposed within a cavity created by a hole in the locking ring 29''''. Preferably, spring clips 37 are made of a flexible metal material such as stainless steel. The device is shown in an unlocked state in FIGS. 16A-B. Each spring clip 37 is wedged into a hole in the locking ring 29'''' in a bent position so that a clinician can pass a suture free end that has been pre-installed at the annulus between the two bottom portions of the spring clip and out through a hole in the top of each spring clip 37. When the locking ring 29'''' is pushed down on the sewing ring 30'''', the device transforms into a locked state as shown in FIGS. 16C-D. In the locked state, each spring clip 37 snaps into a straightened position such that the two bottom portions of the spring clip 37 meet and are forced against each other. Each suture 34 free end is clamped between the two bottom portions of the spring clip 29''''. This prevents each suture 34 from backing out and secures the device to the annulus 11.

Figure 17:
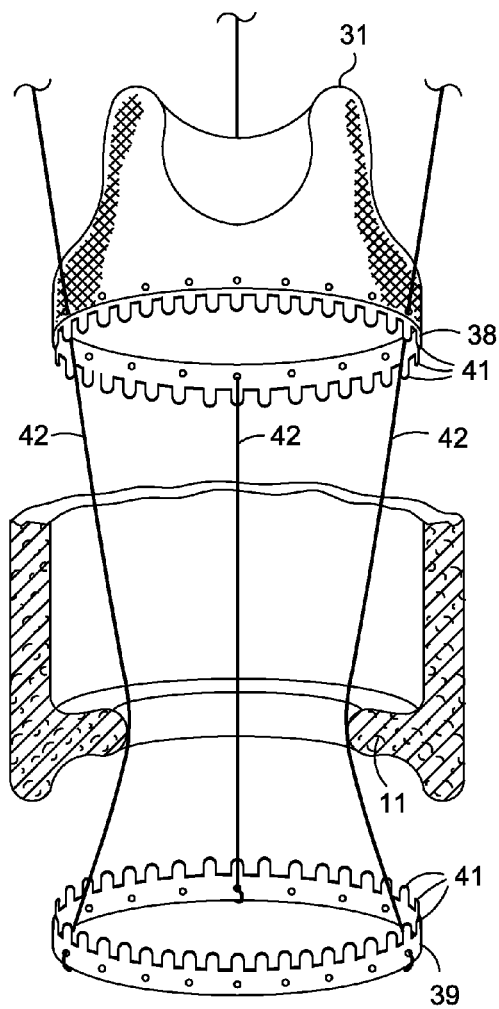
FIG. 17 is a drawing of an anchoring device according to another embodiment of the present invention having mating rings with teeth.

A device according to yet another embodiment is shown in FIG. 17. This device comprises an upper ring 38, a lower ring 39 and connection members 42. In a preferred embodiment, the upper and lower rings are made of a flexible material such as stainless steel. Preferably, the rings are generally circular and have a generally flat bottom profile when viewed from the side. There are teeth 41 on the upper ring 38 and lower ring 39. A prosthetic heart valve 31 is shown attached to the upper ring 38. In a preferred embodiment, the connection members 42 are lengths of suture material made of a synthetic polymeric fiber.

Figure 18:
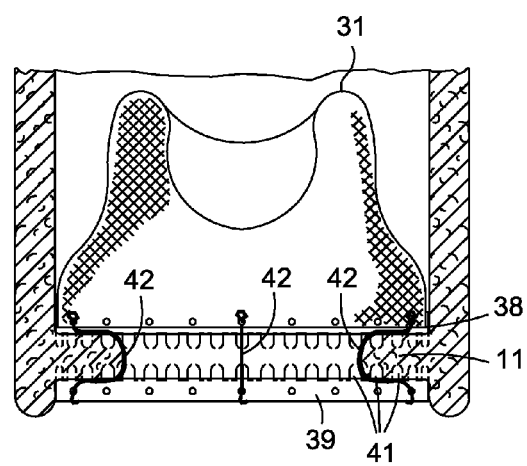
FIG. 18 is a drawing of the device in FIG. 17 after implantation.

To implant the device, a clinician can deform one of the rings and pass it through the annulus of a heart valve. Alternatively, the upper ring 38 or lower ring 39 may be made of a rigid material, and the anchor can be tilted and passed through the annulus sideways, using the natural elasticity of the annulus to facilitate implantation. After this step, the upper ring 38 is on one side of the annulus and the lower ring 39 is on the other side of the annulus. A clinician can pull the connection members 42 to draw the upper ring 38 and the lower ring 39 towards each other to clamp the annulus 11 in between as shown in FIG. 18. Once in place, the connection members 42 can be crimped, snapped, tied, or locked to anchor the device. The teeth 41 help to secure the device in place and prevent leakage around the valve or migration of the valve. Although the teeth 41 are shown axially oriented, they may also be angled slightly outward to more aggressively anchor into the annulus tissue.

Figure 19:
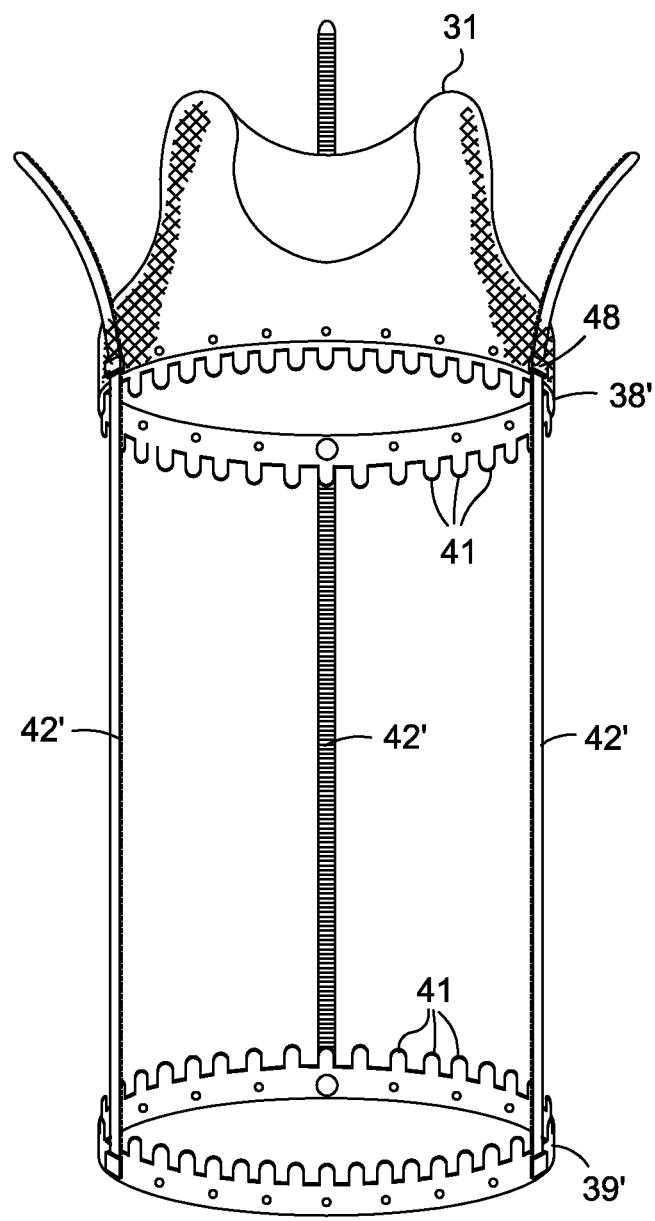
FIG. 19 is a drawing of an alternative device according to another embodiment of the present invention having mating rings with teeth and a ratchet connector.

A device similar to that shown in FIG. 17 but with alternative connection members 42' is shown in FIG. 19. The alternative connection members 42' comprise elongate strips with ratcheting teeth. The connection members 42' are attached to the bottom ring 39'. On the upper ring 38' the connection members 42' pass through receiver housings 48 with ratchet pawls that engage the ratchet teeth, much like cable ties. The ratcheting connection members 42' allow the upper ring 38' to be moved towards the lower ring 39' to clamp on to a heart valve annulus and secure the device in place. The ratcheting connection members 42', while allowing the upper and lower rings to be brought together, resist motion in the opposite direction.

Variations to the devices shown in FIGS. 17 and 18 include using a different type of aggressive or semi-aggressive member or texture on the device to help secure it in place instead of the teeth 41 on the upper ring 38 and lower ring 39. Other variations include using different types of connection members such as wires, or springs. Additionally, the upper and lower rings 38 39 may be made in a shape to better fit a native heart valve annulus. The aortic valve, for example, is made up of three curved sections along which each native leaflet attaches. Instead of being generally circular with a flat bottom profile, the rings could comprise a plurality of curved projections. The curved projections can extend outward from the center of the ring and downward from the bottom of the ring to form a scalloped shape. Thus, each curved projection on the upper and lower ring 38 39 would match up to a corresponding curved portion on a native aortic valve annulus.

A device according to yet another embodiment is shown in FIG. 20. This device is an annuloplasty ring for heart valve repair. The device can be implanted in a native heart valve annulus to reshape the annulus. It comprises an upper ring 43 and a lower ring 44 that snap together to form an annuloplasty ring. The device as shown is shaped to match the native mitral valve annulus, although other shapes may be used depending on the treatment site. The upper ring has a plurality of openings 46 through the body of the ring. Preferably, the openings 46 are slot shaped. The lower ring 44 has plurality of raised portions with grooved or toothed channels 47 that can be inserted into the openings 46 on the upper ring 43.

The device is held in place by a plurality of sutures such as the suture 34 shown in FIG. 20. To implant the device, a clinician passes each suture 34 that has been pre-installed at the annulus through a grooved channel 47 on the lower ring 44. The clinician may then pass the suture 34 through tissue near the implantation site and back out through the grooved channel 47. The grooved channels 47 allow a clinician the flexibility in the placement of each suture 34. Once each suture 34 has been placed, the top ring 43 can be snapped onto the bottom ring 44. The slots in the top ring are sized such that when the top ring 43 is snapped onto the bottom ring 44 the grooved channels 47 are forced closed. Because the free ends of each suture are placed within a grooved channel 47, the sutures are secured when the grooved channels 47 are forced closed.

Figure 21:
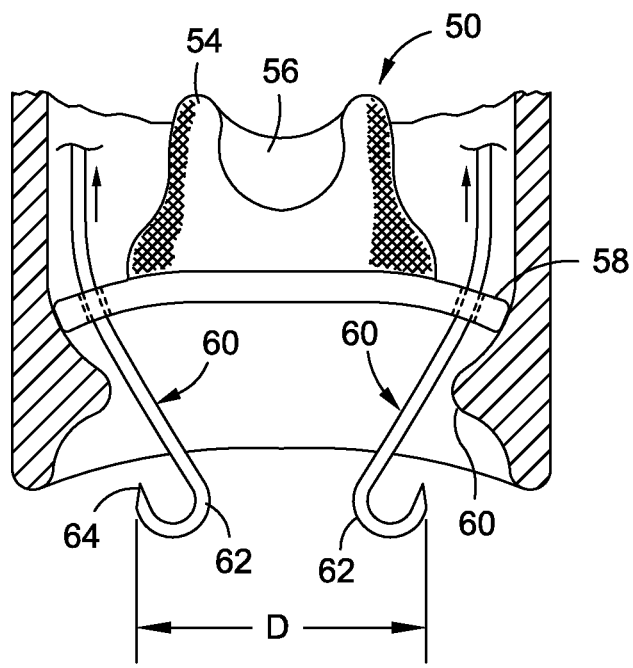
FIGS. 21 and 22 schematically show an alternative system for attaching a prosthetic heart valve to an annulus without the use of sutures using a series of hooks ulled through the valve to engage the annulus.
Figure 22:
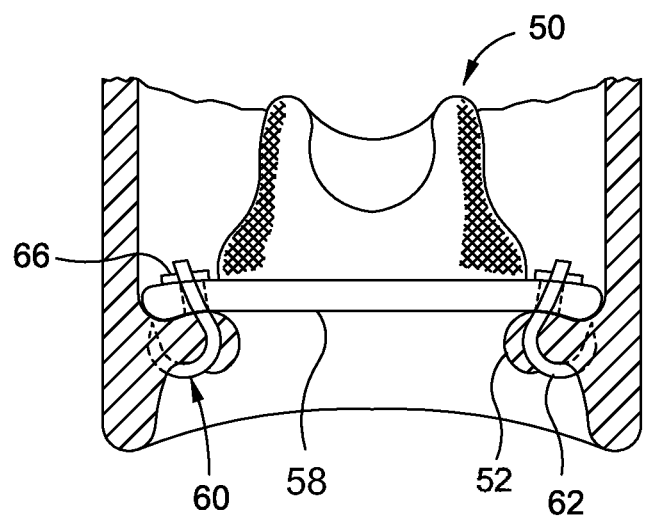

With reference to FIGS. 21 and 22, a prosthetic heart valve 50 is shown being secured to a heart valve annulus 52, such as an aortic annulus, without the use of sutures. The heart valve includes a stent structure having commissures 54 supporting flexible leaflets 56 that provide the occluding surfaces of the valve. A sewing ring or other such soft flange 58 surrounds an inflow end of the stent structure and is sized and shaped to conform to the annulus 52.

A series of elongated hook members 60 passes through the soft flange 58 either through the flange material or through holes preformed therein. Each hook member 60 has a curved distal end 62 terminating in a sharp tip 64. The curved distal ends 62 may be generally circular in curvature, J-shaped, U-shaped, and other shapes. In each embodiment, the sharp tip 64 projects back in the direction of the elongated body of the hook member 60 or may be angled slightly outwardly. In use, the hook members 60 are rotated to that the sharp tips 64 are oriented radially outward. The hook members 60 desirably bend slightly radially inward along their elongated bodies such that the curved distal ends 62 span a maximum diameter D that is smaller than the diameter of the annulus 52, and smaller than the distance across the points at which the hook members 60 pass through the flange 58.

To implant the heart valve 50, the surgeon advances the assembly as seen in FIG. 21 through a number of delivery approaches into the position shown, with the flange just on the outflow side of the annulus 52 and the curved distal ends 62 on the inflow side. The array of curved distal ends 62 circumscribes a circle smaller than the annulus, and thus can be easily inserted therethough from the outflow to inflow side. In any case the elongated hook members 60 are desirably not too rigid so that they may flex inward upon contact with the annulus 52 as they pass therethrough.

Subsequently, as seen in FIG. 22, the series of elongated hook members 60 are pulled proximally through the valve flange 58 so that the curved distal ends 62 engage the annulus. In the illustrated embodiment, the sharp tips 64 pierce the annulus tissue to embed the hook members 60 therein. A small clip 66 or other such device may be applied around each hook member 60 on the top side of the soft flange 58 to secure the hook members 60 in place, after which the tail end of the hook members are trimmed and removed. There should be at least three hook members 60 distributed evenly around the periphery of the valve 50, and more preferably there are at least six; one for each commissure region and one intermediate each commissure region for aortic annuluses. The hook members may be made of a suitable polymer such as nylon, or a metal such as Nitinol or stainless steel. Pledgets (not shown) may also be pre-loaded on the curved distal ends 62 to help prevent the hook members from pulling through the annulus tissue when under tensile load.

FIGS. 23-26 illustrate a further alternative knotless heart valve anchoring system 80 that operates similarly to the system shown in FIG. 19. The system includes a prosthetic heart valve 82 having a leaflet supporting structure 84 and a contoured securing ring 86 around the inflow end thereof in the place and configuration where a sewing ring is usually found. The securing ring 86 has a series of through apertures 88 distributed around its periphery that receive elongated flexible connection members 90 therethrough. Each connection member 90 attaches at a distal end to a lower ring 92, formed in the illustrated embodiment by three ring segments 94a, 94b, 94c. The ring segments 94a, 94b, 94c may be separate or joined with flexible links, as indicated schematically in dashed lines in FIG. 26A. The distal end of each connection member 90 preferably secures to the lower ring 92, but may simply pass downward through apertures 96 therein and have a bead or other such enlargement (not shown) that prevents the connection member from pulling upward through the aperture.

In a preferred embodiment, the connection members 90 comprise elongate strips with ratcheting teeth. The apertures 88 on the securing ring 86 feature ratchet pawls (not shown) that engage the ratchet teeth on the connection members 90, much like cable ties. The ratcheting connection members 90 allow the lower ring 92 to be gradually pulled closer to the securing ring 86 so as to clamp a heart valve annulus therebetween and secure the device in place, as seen in FIG. 25. Specifically, the "supra-annular" securing ring 86 contacts the outflow side of the annulus and the "infra-annular" lower ring 92 contacts the inflow side of the annulus. The ratcheting connection members 90 then resist separation of the rings 86, 92. Alternatively, instead of engaging ratchet teeth, the connection members 90 may be simple sutures that are tied to the lower ring 92 and secured by clamps of some sort in the securing ring 86. For instance, any of the clamping configurations described herein may be used. Further, the connection members 90 may be strip, wire, rod, filament, etc.

With reference in particular to FIGS. 25-26, beneficial details of the securing ring 86 and lower ring 92 are seen. The elevational view of FIG. 25 shows the undulating axial contour of the securing ring 86. The ring 86 includes three peaks 100 alternating with three valleys 102, and generally conforming to an aortic annulus root. This helps match the shape of the ring 86 to the root so as to better clamp to the annulus and also to help eliminate paravalvular leakage. The underside plan view of FIG. 26A shows the non-circular outer peripheral edge of the ring 86 featuring three outward lobe regions 106 alternating with three relief areas 108. The ring 86 thus has a rounded triangular peripheral shape. Again, this helps the ring 86 conform to the aortic root, with the lobe regions 106 projecting into and matching the coronary sinus lobes and the relief areas 108 providing relief for the inwardly-projecting valve commissure regions. The three valleys 102, as seen in FIG. 25, correspond to the lobe regions 106, while the three peaks 100 are centered in the relief areas 108.

The lower ring 92 also generally mimics the undulating shape of the securing ring 86 so as to provide even clamping of the annulus therebetween. As seen in FIG. 26A, the three ring segments 94a, 94b, 94c mostly span the outward lobe regions 106 of the securing ring 86 with breaks at the relief areas 108, which register with the annulus commissures. This segmented assembly for the lower ring 92 serves several purposes. First, the breaks at the annulus commissures avoids clamping at those locations, which is the least flat or even surfaces around the annulus. Secondly, the three segments 94a, 94b, 94c may be inserted separately through the annulus from the outflow to the inflow side, or otherwise collapsed to reduce their aggregate profile, either way permitting the lower ring 92 to be formed on the inflow side of the annulus without difficulty. Finally, the individual segments 94a, 94b, 94c are relatively movable so that they may be separately pulled by the connection members 90 to move both axially and radially relative to the securing ring 86.

The lower ring 92 includes circumferentially-oriented ribs or teeth 110 on its upper surface. In the illustrated embodiment, each segment 94a, 94b, 94c has three rows of teeth 110 that angle slightly inwardly. These rows of teeth 110 help anchor the valve 82 to the annulus, as will be described below. Each segment 94a, 94b, 94c further has a plurality of outwardly-projecting fingers 112 that are rounded so as not to pierce tissue but nonetheless help anchor the structure.

Figure 23:
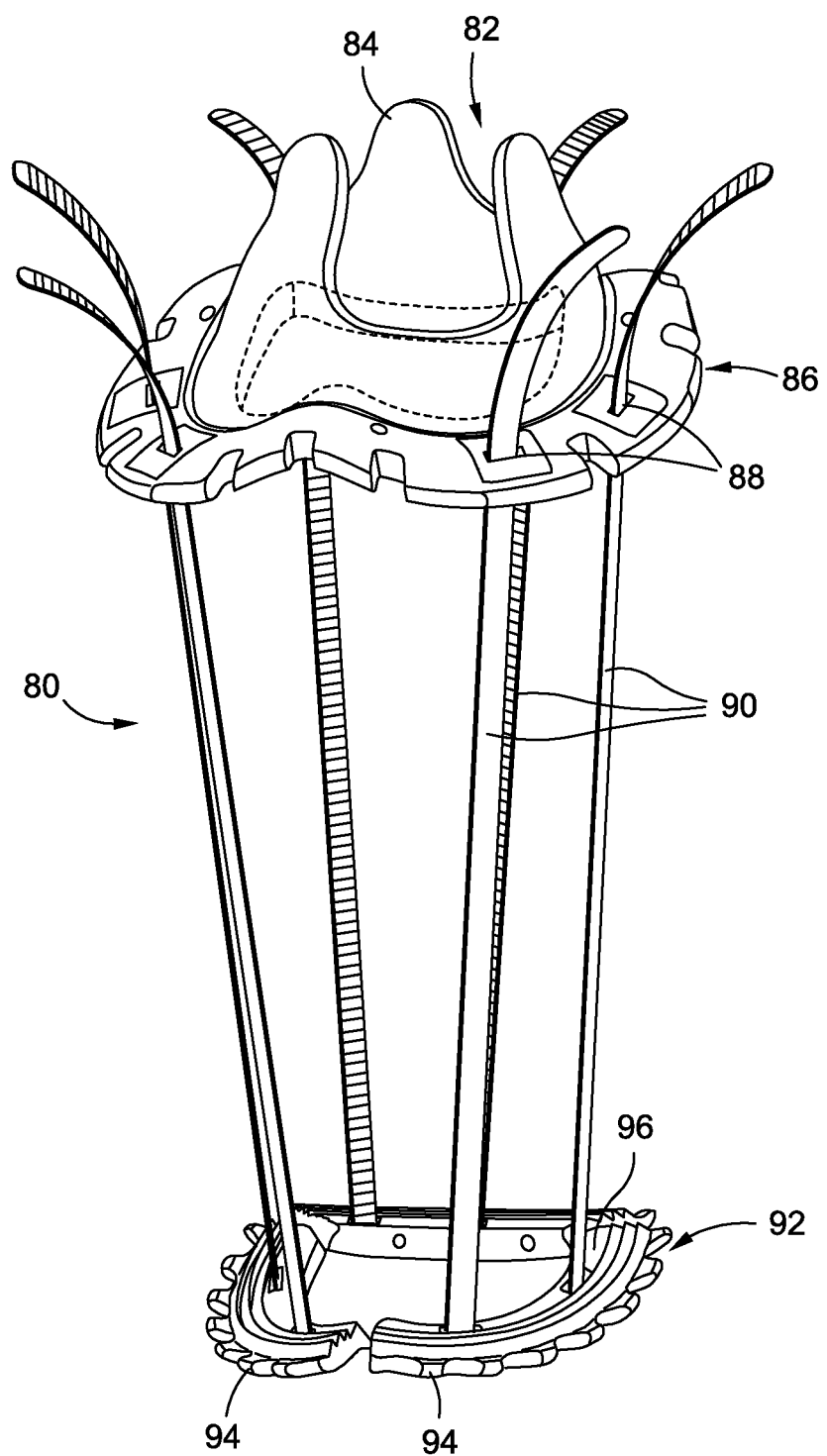
Figure 24:
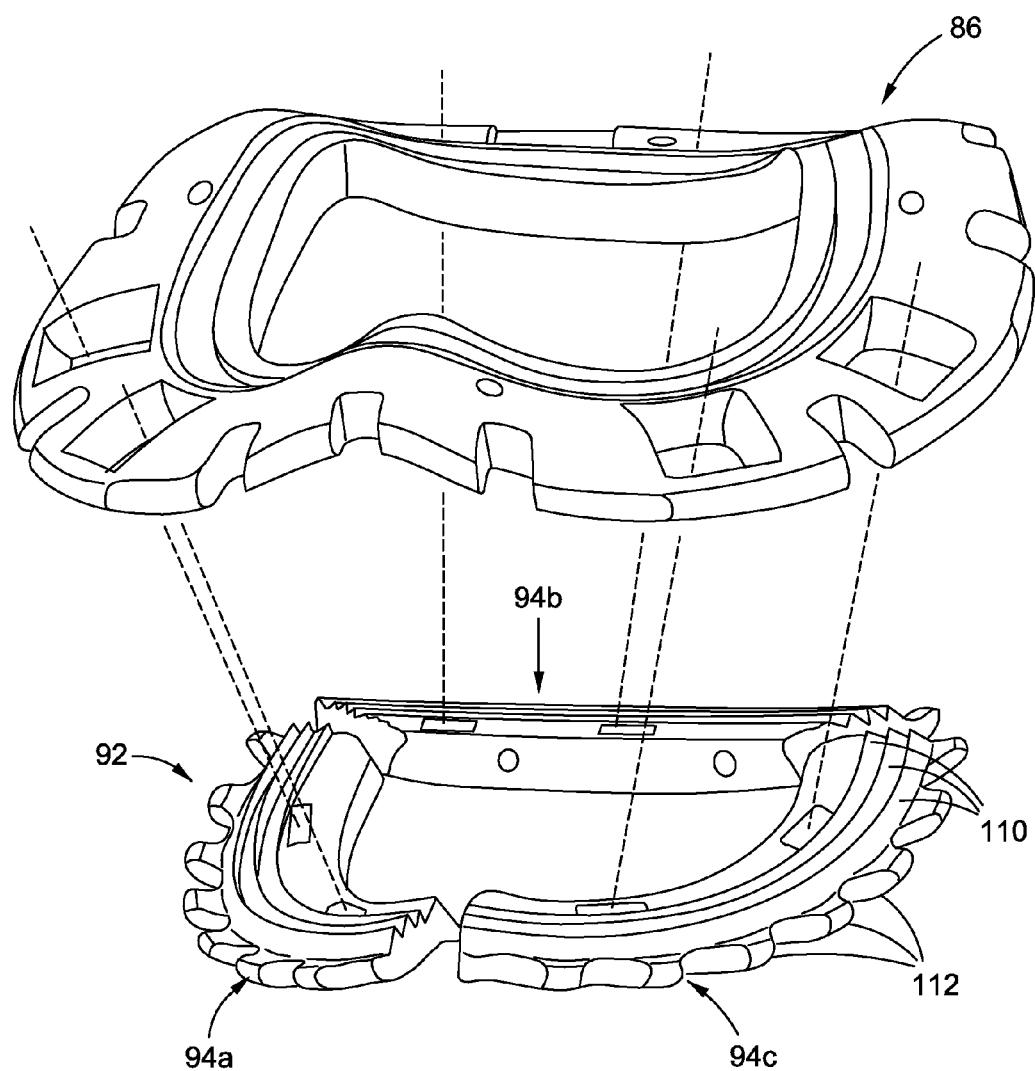

In use, the surgeon advances the collapsed lower ring 92 (or each three segment 94a, 94b, 94c separately) through the aortic annulus from the outflow to the inflow side. Tail ends 114 of the connection members 90 extend up from the annulus and are threaded through the apertures 88 distributed around the securing ring 86 periphery. In a preferred embodiment, as seen in FIG. 23 and also in dashed line in FIG. 24, the connection members 90 are more closely spaced at the lower ring 92 then at the securing ring 86 so as to form a conical array. In a preferred embodiment, there are at least one, and preferably two connection members 90 associated with each three lower segments 94. Pulling on the tail ends 114 applies tension to the connection members to draw the two rings 86, 92 toward one another and clamp them around the annulus. As with earlier embodiments, the tail ends 114 are then trimmed off in a final step before closing the affected access passages and incisions. Since the lower ends of the connection members 90 are radially inward from the apertures 88 in the securing ring 86, and due to the segmented nature of the ring 92, pulling the connection members 90 displaces the three segments 94a, 94b, 94c both axially upward and radially outward. The rows of teeth 110 grab the annulus tissue and help cinch the assembly together. The outer rows of projecting fingers 112 frictionally engage the surrounding anatomy on the underside of the annulus and help retain the assembly from rotation about the flow axis.

The "supra-annular" securing ring 86 and the "infra-annular" lower ring 92 may be molded of a suitable polymer, such as nylon or Delrin. Alternatively, they may be machined from a suitable metal such as stainless steel. One or both may also be surrounded with a fabric covering to help tissue ingrowth.

While embodiments and applications of this invention have been shown and described, it would be apparent to those skilled in the art that many more modifications are possible without departing from the inventive concepts herein, and it is to be understood that the words which have been used are words of description and not of limitation. Therefore, changes may be made within the appended claims without departing from the true scope of the invention.

What is claimed is:

1. A knotless heart valve prosthesis, comprising:
a lower segmented ring having an implanted size that can be collapsed to a smaller size for passage through an annulus, the lower segmented ring comprising three separate segments arranged in a circumferential array with gaps therebetween;
an upper securing ring;
a prosthetic heart valve connected to the securing ring; and
a plurality of elongated flexible connection members extending upward from the lower segmented ring through mating apertures formed in the securing ring so as to couple the two rings together and clamp a valve annulus therebetween.

2. The prosthesis of claim 1, further including a plurality of protruding members that extend generally radially outward from the lower segmented ring that help anchor the heart valve to the valve annulus.

3. The prosthesis of claim 1, wherein the lower segmented ring includes rows of teeth on an upper surface thereof that help anchor the heart valve to the valve annulus.

4. The prosthesis of claim 1, wherein the connection members are more closely spaced at the lower segmented ring than at the securing ring.

5. The prosthesis of claim 1, further including flexible links joining the three separate segments of the lower segmented ring.

6. The prosthesis of claim 1, wherein the connection members comprise elongate strips with ratcheting teeth, and the mating apertures in the securing ring include ratchet pawls that engage the ratchet teeth on the connection members.

7. The prosthesis of claim 1, wherein the connection members comprise sutures, and the mating apertures in the securing ring comprise suture clamps.

8. The prosthesis of claim 1, wherein the securing ring has an undulating contour with three axially elevated peaks intermediate three axial valleys, and wherein the lower segmented ring mimics the undulating contour of the securing ring and has three segments that correspond to the three axially valleys of the securing ring, and wherein there are at least two connection members extending upward from each segment of the lower segmented ring.

9. A knotless aortic heart valve prosthesis, comprising:
a prosthetic heart valve having a securing ring extending outward from an inflow end thereof, the securing ring having an undulating contour with three outwardly projecting lobes intermediate three radially inward relief areas, the relief areas defining axial peaks and the lobes defining axial valleys, the securing ring having apertures therethrough;
a lower segmented ring smaller in circumference than the securing ring and having an undulating shape that mimics the undulating contour of the securing ring, the lower segmented ring comprising three separate segments arranged in a circumferential array with gaps therebetween; and
a plurality of elongated flexible connection members extending upward from the lower segmented ring through the apertures formed in the securing ring so as to couple the two rings together and clamp a valve annulus therebetween.

10. The prosthesis of claim 9, further including a plurality of protruding members that extend generally radially outward from the lower segmented ring that help anchor the heart valve to the valve annulus.

11. The prosthesis of claim 9, wherein the lower segmented ring includes rows of teeth on an upper surface thereof that help anchor the heart valve to the valve annulus.

12. The prosthesis of claim 9, wherein the connection members are more closely spaced at the lower segmented ring than at the securing ring.

13. The prosthesis of claim 9, further including flexible links joining the three separate segments of the lower segmented ring.

14. The prosthesis of claim 9, wherein the connection members comprise elongate strips with ratcheting teeth, and the apertures in the securing ring include ratchet pawls that engage the ratchet teeth on the connection members.

15. The prosthesis of claim 9, wherein the connection members comprise sutures, and the apertures in the securing ring comprise suture clamps.

16. A knotless heart valve prosthesis, comprising:
   a lower segmented ring having an implanted size that can be collapsed to a smaller size for passage through an annulus;
   an upper securing ring having an undulating contour with three axially elevated peaks intermediate three axial valleys, and wherein the lower segmented ring mimics the undulating contour of the securing ring and has three segments that correspond to the three axially valleys of the securing ring;
   a prosthetic heart valve connected to the securing ring; and
   a plurality of elongated flexible connection members extending upward from the lower segmented ring through mating apertures formed in the securing ring so as to couple the two rings together and clamp a valve annulus therebetween, and wherein there are at least two connection members extending upward from each segment of the lower segmented ring.

17. The prosthesis of claim 16, further including a plurality of protruding members that extend radially outward from the lower segmented ring that help anchor the heart valve to the valve annulus.

18. The prosthesis of claim 16, wherein the lower segmented ring includes rows of teeth on an upper surface thereof that help anchor the heart valve to the valve annulus.

19. The prosthesis of claim 16, wherein the connection members comprise elongate strips with ratcheting teeth, and the apertures in the securing ring include ratchet pawls that engage the ratchet teeth on the connection members.

20. The prosthesis of claim 16, wherein the connection members comprise sutures, and the mating apertures in the securing ring comprise suture clamps.

* * * * *